(12) United States Patent  
Cimino

(10) Patent No.: US 7,361,172 B2
(45) Date of Patent: Apr. 22, 2008

(54) ULTRASONIC DEVICE AND METHOD FOR TISSUE COAGULATION

(75) Inventor: William C. Cimino, Louisville, CO (US)

(73) Assignee: Sound Surgical Technologies LLC, Louisville, CO (US)

(*) Notice: Subject to any disclaimer, the term of this patent is extended or adjusted under 35 U.S.C. 154(b) by 256 days.

(21) Appl. No.: 10/455,486

(22) Filed: Jun. 4, 2003

(65) Prior Publication Data

US 2004/0102801 A1 May 27, 2004

Related U.S. Application Data

(60) Provisional application No. 60/386,119, filed on Jun. 4, 2002.

(51) Int. Cl.
*A61B 18/04* (2006.01)

(52) U.S. Cl. .............................. 606/27; 606/1; 606/40; 606/49; 601/2; 601/3

(58) Field of Classification Search .................. 606/37, 606/40
See application file for complete search history.

(56) References Cited

U.S. PATENT DOCUMENTS

| | | | |
|---|---|---|---|
| 2,714,890 A | 8/1955 | Vang | |
| 2,845,072 A | 7/1958 | Shafer | 128/303.14 |
| 3,053,124 A | 9/1962 | Balamuth et al. | |
| 3,526,219 A | 9/1970 | Balamuth | |
| 3,636,943 A | 1/1972 | Balamuth | 128/24 |
| 3,657,056 A | 4/1972 | Winston et al. | 156/580.2 |
| 3,752,161 A | 8/1973 | Bent | 606/169 |
| 3,792,701 A | 2/1974 | Kloz et al. | 128/7 |
| 3,862,630 A | 1/1975 | Balamuth | |
| 3,899,829 A | 8/1975 | Storm et al. | 606/169 |
| 4,375,961 A | 3/1983 | Brooks | 433/4 |
| 4,491,132 A | 1/1985 | Aikins | |

(Continued)

FOREIGN PATENT DOCUMENTS

DE 2032501 1/1972

(Continued)

OTHER PUBLICATIONS

Spivak, H.; Richardson, W.; Hunter, J.; "The use of bipolar cautery, laparosonic coagulating shears, and vascular clips for hemostasis of small and medium-sized vessels,"Surgical Endoscopy Feb. 1998; 12(2):183-5.

(Continued)

*Primary Examiner*—Brian L. Casler
*Assistant Examiner*—James Kish
(74) *Attorney, Agent, or Firm*—René A. Pereyra; Merchant & Gould P.C.

(57) ABSTRACT

An ultrasonic surgical device for the coagulation of animal tissue having an ultrasonic applicator and a movable jaw with a jaw surface adjacent the distal portion of the ultrasonic applicator for movement toward the applicator to a closed position at a predefined clearance of between about 0.075 to about 1.9 millimeters from the applicator. The device may also include a mechanical cutting element that can be extended into the clearance to cut the tissue and means to vary the predefined clearance without removing the applicator from the patient. Tissue coagulating and cutting can be maximized and performed separately and can be easily monitored by the surgeon.

26 Claims, 6 Drawing Sheets

U.S. PATENT DOCUMENTS

| | | | |
|---|---|---|---|
| 4,497,320 A | 2/1985 | Nicholson et al. | |
| 4,655,216 A | 4/1987 | Tischer | |
| 4,674,500 A | 6/1987 | DeSatnick | |
| 4,723,545 A | 2/1988 | Nixon et al. | 128/305 |
| 4,733,662 A | 3/1988 | DeSatnick et al. | 606/171 |
| 4,825,865 A | 5/1989 | Zelman | 128/303.1 |
| 4,832,683 A | 5/1989 | Idemoto et al. | 604/22 |
| 4,877,026 A | 10/1989 | de Laforcade | 604/22 |
| 5,057,199 A | 10/1991 | Lievens et al. | |
| 5,059,210 A | 10/1991 | Clark et al. | 428/680 |
| 5,123,903 A | 6/1992 | Quaid et al. | |
| 5,147,357 A | 9/1992 | Rose et al. | 606/52 |
| 5,167,725 A | 12/1992 | Clark et al. | 428/680 |
| 5,201,759 A | 4/1993 | Ferzli | 606/170 |
| 5,217,460 A | 6/1993 | Knoepfler | 606/52 |
| 5,263,957 A | 11/1993 | Davison | 606/171 |
| 5,322,055 A * | 6/1994 | Davison et al. | 601/2 |
| 5,324,299 A | 6/1994 | Davison et al. | 606/167 |
| 5,322,055 A | 10/1997 | Davison et al. | 601/2 |
| 5,797,939 A | 8/1998 | Yoon | 606/167 |
| 5,873,873 A * | 2/1999 | Smith et al. | 606/1 |
| 6,004,335 A | 12/1999 | Vaitekunas et al. | 606/169 |
| 6,036,667 A | 3/2000 | Manna et al. | 604/22 |
| 6,193,709 B1 | 2/2001 | Miyawaki et al. | 606/1 |
| 6,352,532 B1 | 3/2002 | Kramer et al. | 606/41 |
| 6,458,130 B1 * | 10/2002 | Frazier et al. | 606/51 |
| 6,569,178 B1 * | 5/2003 | Miyawaki et al. | 606/169 |
| 2001/0025184 A1 | 9/2001 | Messerly | 606/169 |
| 2001/0029315 A1 | 10/2001 | Sakurai et al. | 600/101 |
| 2001/0041828 A1 | 11/2001 | Dockman et al. | 600/232 |
| 2001/0047182 A1 | 11/2001 | Banko | 606/169 |
| 2002/0002376 A1 | 1/2002 | Gannoe et al. | 606/167 |
| 2002/0002378 A1 | 1/2002 | Messerly | 606/169 |
| 2002/0002379 A1 | 1/2002 | Bishop | 606/169 |
| 2002/0002380 A1 | 1/2002 | Bishop | 606/169 |
| 2002/0019646 A1 | 2/2002 | Mastri et al. | 606/169 |
| 2002/0026184 A1 | 2/2002 | Witt et al. | 606/40 |
| 2002/0029060 A1 | 3/2002 | Hogendijk | 606/185 |
| 2003/0055417 A1 * | 3/2003 | Truckai et al. | 606/27 |

FOREIGN PATENT DOCUMENTS

| | | |
|---|---|---|
| DE | 7705947 | 6/1977 |
| FR | 2 355 521 | 2/1978 |
| JP | 61-128954 | 6/1986 |
| JP | 232948 | 9/1989 |
| SU | 737735 | 5/1980 |
| WO | PCT/US03/17677 | 6/2003 |

OTHER PUBLICATIONS

Landman, J. et al., "Comparison of the Ligasure System, Bipolar electrosurgery, Harmonic scalpel, titanium clips, Endo-FIA, and sutures for laparoscopicvascular control in a porcine model," Presensted at SAGES meeting, poster session, St. Louis, MO. Apr. 19-Apr. 21, 2001.
PCT Written Opinion for PCT/US03/17677 dated Jun. 17, 2004.
PCT International Preliminary Examination Report dated Oct. 28, 2005.
Supplementary European Serach Report for EP 03 73 6854 dated Oct. 5, 2007.
Office Action in Chinese Counterpart Application No. 03818709.4; Jun. 2, 2006.
Office Action in Australian Counterpart Application No. 2003237398; Sep. 18, 2007.

* cited by examiner

ULTRASONIC DEVICE AND METHOD FOR TISSUE COAGULATION

This application claims the benefit of priority from U.S. provisional patent application Ser. No. 60/386,119, filed Jun. 4, 2002.

I. FIELD OF THE INVENTION

The present invention relates generally to surgical instruments, and more particularly, to an ultrasonic surgical device for use in coagulation of tissues of a patient.

II. BACKGROUND OF THE INVENTION

Hemostasis of bleeding or potentially bleeding tissues is of premium importance in open or laparoscopic surgery. Several methods are currently used to coagulate tissues to achieve the desired hemostasis. Sutures are safe, reliable, and commonly used on larger vessels or structures, but are difficult to use on small vessels or structures or in situations involving diffuse bleeding. Monopolar electrosurgery works by electrically heating and burning the tissue to achieve coagulation. It is effective on the smaller vessels and structures but may cause undesirable thermal trauma to adjacent tissues due to stray electrical conduction in a wet surgical environment. Bipolar electrosurgery also works by electrically heating the tissues and provides improved control of stray electrical conduction relative to monopolar electrosurgery. Bipolar instruments may suffer from tissue adherence to the electrodes, causing the coagulated tissue to be re-opened and bleed again as the probes are removed. Ultrasonic instruments use frictional heat generated by rapid vibration rubbing of the tissue to create hemostasis.

Ultrasonic surgical devices for cutting and coagulation of tissue are known. All of these devices utilize longitudinal vibrations in an ultrasonic member to accomplish a desired surgical effect such as cutting with simultaneous coagulation. Clamping mechanisms have been disclosed which claim to improve cutting and coagulation performance by enhancing the tissue contact between the vibrating member and the clamp surface. U.S. Pat. Nos. 3,862,630 and 3,636,943, both to Balamuth, disclose two types of ultrasonic surgical devices: a first device for simultaneously cutting and coagulating tissue, and a second device for joining together layers of tissue. The device for joining together layers of tissue has a vibrating ultrasonic member and a clamp mechanism, the working surface of the clamp mechanism being perpendicular to the direction of the longitudinal vibrations of the tool, so that tissues are compressed between the working surface of the clamp and the end surface of the vibrating ultrasonic member. This "end-on" design blocks tissue access to the clamped region between the ultrasonic member and clamp mechanism from the axial direction, requiring that tissue be accessed laterally, and thereby severely limits application of the device for surgical application because tissue cannot be accessed in a scissor-like fashion.

U.S. Pat. No. 5,322,055 to Davidson discloses an ultrasonic surgical device for simultaneously cutting and coagulating tissue having a vibrating ultrasonic member and a clamp mechanism, the ultrasonic member having a surgical blade with an elongated edge parallel to the axis of longitudinal vibration at the distal end of the vibrating ultrasonic member. This patent alleges enhanced cutting performance due to the surgical blade with the elongated edge and also improves performance by providing tissue access to the ultrasonic member and the clamp mechanism from the axial direction. The clamp mechanism is designed to close completely (i.e., touch) against the vibrating ultrasonic member to achieve the described cutting and coagulation effects. The improved cutting action in this design is allegedly caused by the vibration of the surgical blade with an elongated edge and the complete closure of the blade against the clamp mechanism.

U.S. Pat. No. 6,193,709 to Manna discloses an ultrasonic surgical device for simultaneously cutting and coagulating tissue having a vibrating ultrasonic member and a clamp mechanism, the ultrasonic member having a blade at the distal end of the vibrating ultrasonic member, the blade forming an acute angle with respect to the axis of longitudinal vibration. The patent alleges that the angled design enhances tissue contact between the clamp mechanism and the blade during operation and thereby improves performance. The clamp mechanism is designed to close completely (touch) against the vibrating ultrasonic member to achieve the described cutting and coagulation effects. Improved cutting action in this design is due to the vibration of the blade with the acute angle with respect to the axis of longitudinal vibration and the complete closure of the blade against the clamp mechanism.

U.S. Pat. No. 6,193,709 to Miyawaki discloses an ultrasonic surgical device for treatments such as incision and coagulation having a vibrating ultrasonic member and a clamp having a follow-up mechanism so that the clamp can follow a deflective displacement of the distal end portion of the vibrating ultrasonic member. This patent asserts that the follow-up mechanism eliminates potential gaps between the vibrating ultrasonic member and the clamp mechanism as the clamp mechanism is closed onto the vibrating ultrasonic member, thereby improving grasping and treatment performance. The clamp mechanism is designed to close completely (i.e., touch) against the vibrating ultrasonic member to achieve the described treatments such as incision and coagulation.

None of the patents discloses a device for limiting the closure of the clamp mechanism relative to the vibrating ultrasonic member for the purpose of creating a predetermined clearance there between so that an improved coagulation effect is achieved. Holding the clamp against the ultrasonic member in the prior art devices will inevitably result in the cutting of the tissue. The surgeon has no way of knowing how far the process has occurred from the intended coagulation to undesirable cutting. Indeed, these prior art devices are designed to achieve simultaneous cutting and coagulation as the clamp closes completely against the vibrating ultrasonic member, regardless of the shape of the jaw surface of the clamp mechanism and the shape of the vibrating ultrasonic member. It is often desirable in the course of surgery to coagulate tissue without cutting. It is impossible to reliably separate these two processes in the prior art devices. Thus, there is a need to improve the coagulation performance of ultrasonic surgical devices and further to provide independent cutting and coagulation capabilities.

Deficiencies in the performance of prior art coagulation devices have been noted in the literature. (See, for example, Spivak H. et al., "The Use of Bipolar Cautery, Laparsonic Coagulating Shears, and Vascular Clips for Hemostatis of Small and Medium-sized Vessels," *Surgical Endoscopy*, 12(2):183-85 (February 1998) and Landman, J. (Washington University), "Comparison of the Ligasure System, Bipolar Electrosurgery, Harmonic Scalpel, Titanium Clips, Endo-GIA, and Sutures for Laparoscopic Vascular Control in a Porcine Model," presented at the *Society of American Gastrointestinal Endoscopic Surgeons,* St. Louis, Mo., (Apr. 10-21, 2001). Both of these studies included the ultrasonic laparosonic coagulating shears ("LCS") manufactured and distributed by Johnson & Johnson using technology believed to be covered by the Davidson '055 Patent referenced above. Spivak et al. tested the capability of the LCS device and others to coagulate small and medium sized blood vessels in pigs by increasing the associated blood pressure to the point of failure or a maximum load of 300 mm. Hg. While the authors personally concluded that the devices "can be considered safe," the devices were not uniformly successful. The LCS device was successful in all of the "small vessel" tests but had two complete failures in the twelve tests of medium-sized vessels and two additional instances where the medium-sized vessel commenced bleeding before the defined pressure limit was reached. This is an unacceptable failure rate of 33%. As noted by the authors, the LCS needs to be properly sized and the surgeon properly trained in order to use the LCS successfully on medium-sized vessels. In addition, the authors recommended that "the surgeon have a good alternative method in case initial hemostasis fails." Similarly, Landman compared various modalities for sealing vessels. On arteries, the LCS succeeded 5/6 times for an 83% success rate; on veins the LCS succeeded 3/6 times for a 50% success rate. Thus, there is clearly a need for significant improvement in a surgical coagulation device.

A means to substantially improve the coagulation performance of ultrasonic surgical instruments has now been discovered. First, the coagulation performance can be improved by separating the coagulation and cutting functions of the instrument so that they are done sequentially rather than simultaneously. Indeed, it has proven helpful to perform the coagulation prior to the cutting rather than simultaneously or in the opposite order. A sequential approach allows time for the tissue to be coagulated and cooled so that it sets before any cutting action occurs. Indeed, tissue bleeding may be totally avoided in this manner. The present invention accomplishes the sequential coagulating and cutting steps with a single grasp of the instrument, meaning that the tissue grasp does not have to be released to alter the instrument for cutting purposes once coagulation is achieved. Second, the coagulation performance is substantially improved by providing a predefined clearance between a jaw surface and a vibrating ultrasonic applicator so that a tissue flow will occur in a carefully controlled manner. The "tissue flow" (i.e., the propensity of the tissue to move plastically upon sufficient heating) in the predefined clearance creates a zone of coagulated tissue that is much less likely to re-bleed than tissue that is simultaneously cut and coagulated with previously disclosed methods. It has now been discovered that if the predefined clearance is carefully controlled to be between about 0.075 to about 1.9 millimeters, and preferably between about 0.075 and about 0.75 millimeters, then the most effective coagulation performance is obtained. It has been found that if the predefined clearance is less than about 0.075 mm, simultaneous cutting action may occur. If the predefined clearance is greater than about 1.9 mm, it has been found that insufficient tissue flow is achieved and complete coagulation may not occur.

III. SUMMARY OF THE INVENTION

The present invention provides a novel, improved ultrasonic surgical device for and method for coagulating tissue. The device of the present invention has a surgical handle with an ultrasonic transducer mounted therein for generating ultrasonic vibrations. An ultrasonic applicator is attached to the ultrasonic transducer for transmitting longitudinal ultrasonic vibrations and extends distally from the surgical handle. The ultrasonic applicator is generally and substantially round in cross-section at the distal end and has a diameter between approximately 2 millimeters and 6 millimeters. A clamp with a jaw surface is supported on an elongated support member that is releasably attached to the surgical handle that generally surrounds the ultrasonic applicator along its length. The clamp and jaw surface are designed so that the clamp cannot be completely closed against the vibrating ultrasonic applicator, but is stopped at a predefined clearance, i.e., distance between the jaw surface and the vibrating ultrasonic applicator. This predefined clearance provides a zone for controlled tissue flow as the vibrating ultrasonic member heats the tissue. The shape and thickness of the predefined clearance determine the quality and final shape of the coagulated tissue. The predefined clearance may be varied between between about 0.075 to about 1.9 mm, and preferably between about 0.075 and about 0.75 mm, depending on the type and structure of the targeted tissue to be coagulated. The surgical device can include means for adjusting the clearance within this range. Thus, the vibrating ultrasonic applicator is not a vibrating "blade" and is not used for the cutting of tissues, but only for improved coagulation. The zone of controlled tissue flow also contributes to improved coagulation by creating an improved coagulation effect and by avoiding simultaneous cutting during coagulation. The thickness and shape of the tissue flow is carefully controlled.

If a cutting capability is desired with the surgical device, a separate non-ultrasonic cutting element may be provided that can be advanced and retracted to accomplish the cutting function as a separate step. The cutting element may be advanced after the coagulation has been completed, and the jaw is still closed to the maximum permitted extent. Preferably, the cutting element may be a surgical blade with a sharpened leading edge that cuts the coagulated tissue as it is advanced. Other forms of mechanical cutting tools can be employed. The surgeon can wait to advance the cutting tool until sufficient time has elapsed for the tissue to have been coagulated and "cooled" to minimize bleeding during the cutting process.

The device of the present invention may also be employed in an improved method of coagulation comprising the application of ultrasonic surgery via an applicator having a round cross-section to tissue held by a clamp located at a fixed distance from the applicator's surface. A surgical method may also be employed using that coagulation method to coagulate or cauterize tissue prior to cutting with a mechanical cutting tool attached to, but separate from, the ultrasonic applicator.

Thus, the present invention provides an improved ultrasonic surgical instrument and method for tissue coagulation alone or with a separate cutting of tissue. To accomplish this, the present invention includes an ultrasonic surgical instrument and method with a predetermined clearance between the surfaces of a clamp holding the tissue against a vibrating ultrasonic member having a substantially circular cross-section so that controlled flow of the tissue can occur without ultrasonic cutting. In addition, the present invention includes an ultrasonic surgical instrument and method where the cutting means is contained in the same instrument but is independent of the ultrasonic vibrations. Other features or variations of the present invention for improved coagulation may be apparent to one skilled in the art from the enclosed specification, drawings and claims.

The invention may be best understood by reference to the detailed description of some preferred embodiments and the illustrations of preferred embodiments in the accompanying figures.

IV. BRIEF DESCRIPTION OF THE DRAWINGS

The following drawings show specific embodiments that help appreciate the novel features of the present invention.

Figure 1A:
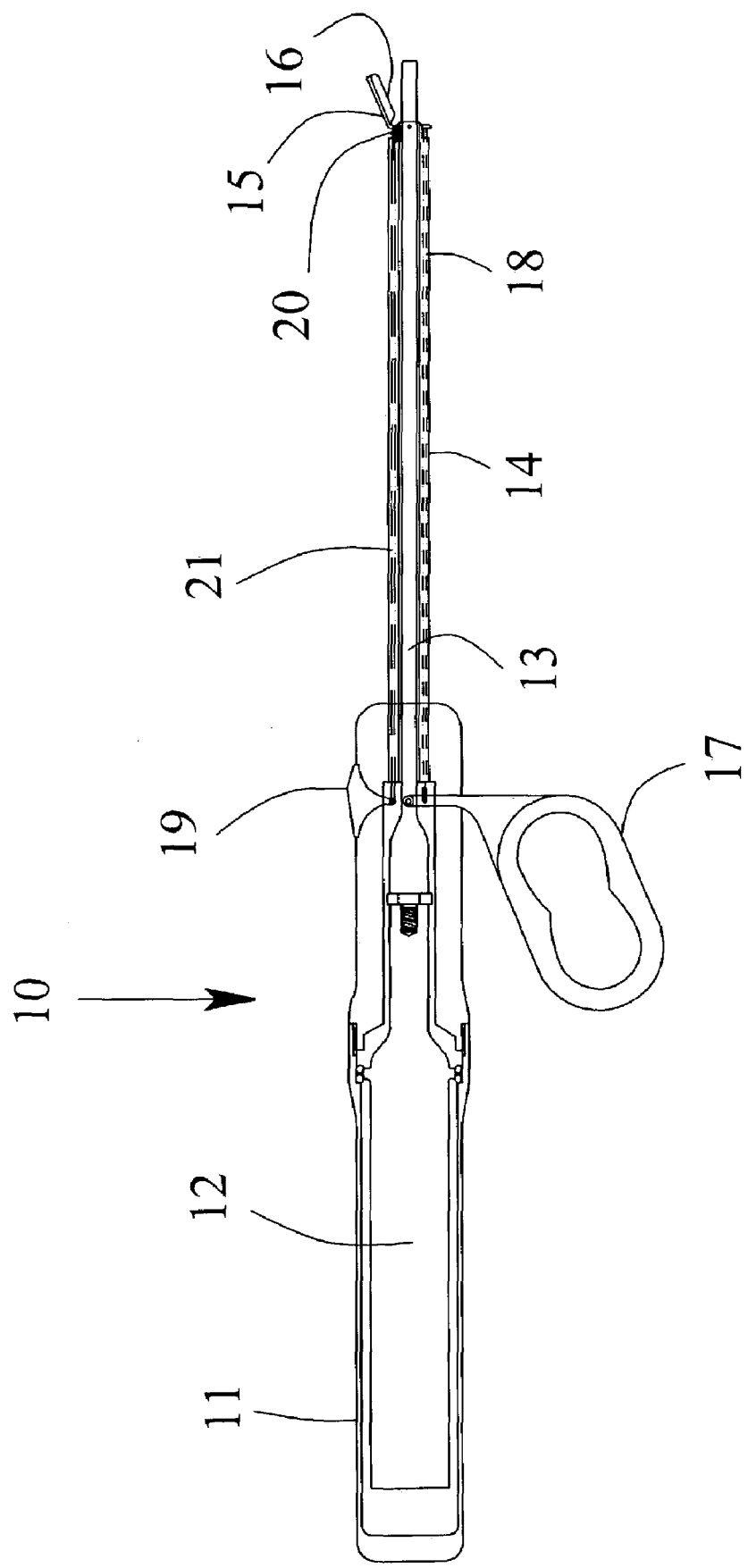
FIG. 1a is a partial cut-away, side-view of one embodiment of the device of the present invention. The drawing depicts the device with the clamp in an open position and the mechanical cutting tool in a retracted position.

Common reference numerals have been used on all drawings for convenience.

V. DETAILED DESCRIPTION

Referring to the drawings, FIG. 1a is a schematic representation of one preferred embodiment of the invention. FIG. 1 illustrates a partial cut-away view of the present invention including an ultrasonic surgical instrument, generally designated 10. The instrument has a surgical handle 11 to be held and manipulated by the surgeon. The surgical handle 11 may be fabricated from either machined or molded plastic components. An ultrasonic transducer 12 is mounted within the surgical handle 11 for generating ultrasonic vibrations. The ultrasonic vibrations may be generated using any common and well-known means such as the use of PZT crystals held in compression.

An ultrasonic applicator 13 is attached to the ultrasonic transducer 12 and extends distally from the ultrasonic transducer 12. The preferred method of attachment is a threaded joint. The ultrasonic applicator may be fabricated from any suitable metallic material including, for example, titanium alloys, aluminum alloys, or stainless steel alloys. The preferred material is titanium alloy Ti6Al4V. Standard machining processes such as lathe or mill processes can be used.

As mentioned previously, ultrasonic applicators employed in the present invention are generally round in cross-section at the point of application of energy to the tissue. These applicators do not have edges that would focus and disseminate ultrasonic energy in a manner promoting cutting, but instead are designed to provide energy in a uniform manner consistent exclusively with the coagulation of tissue. Indeed, cutting functionality, if needed, is provided in a separate mechanical component of the surgical instrument to avoid compromising the design of the ultrasonic applicator.

The combined length of the ultrasonic transducer 12 and the ultrasonic applicator 13 must be designed to have the desired resonant frequency of vibration. The range of vibration frequencies is generally 20 kHz to 60 kHz. Any vibration frequency in this range can be utilized.

An elongated support member 14 is releasably attached to the surgical handle 11 and generally surrounds the ultrasonic applicator 13 along its length. The elongated support member 14 may be fabricated from metal or plastic materials. The preferred material is plastic such as DelrinR (acetyl copolymer) or "ABS" (acrylonitrile-butadiene-styrene). A clamp 15 with a jaw surface 16 is supported on the distal end of the elongated support member 14. The clamp may be fabricated from metal or plastic using either standard machining processes or standard molding process (metal or plastic). The preferred method and material is a molded metal clamp mechanism as this provides for maximum stiffness of the part and the best clamping performance. The jaw surface 16 may have a variety of cross-sectional shapes, for example, those depicted in FIGS. 3a-3c. The jaw surface 16 may also have a serrated or grooved surface to improve grasping performance.

The clamp 15 may be opened and closed relative to the side of the ultrasonic applicator 13. In FIG. 1a, the clamp is depicted in the open position. An actuation handle 17 is connected to the surgical handle 11 and is used to actuate the clamp 15 between the open and closed positions. A clamp transmission rod 18 connects the actuation handle 17 and the clamp 15.

An actuation slider 19 is connected to the surgical handle 11 and is used to advance and retract a cutting element 20 in a direction parallel or generally parallel to the ultrasonic applicator. The cutting element 20 may be a stainless steel blade or a formed cutting shape on the end of a blade connecting rod 21. The blade connecting rod 21 connects the actuation slider 19 and the cutting element 20. The connecting rod 21 is preferably fabricated from stainless steel wire that can be soldered or welded to the cutting element 20.

Figure 1B:
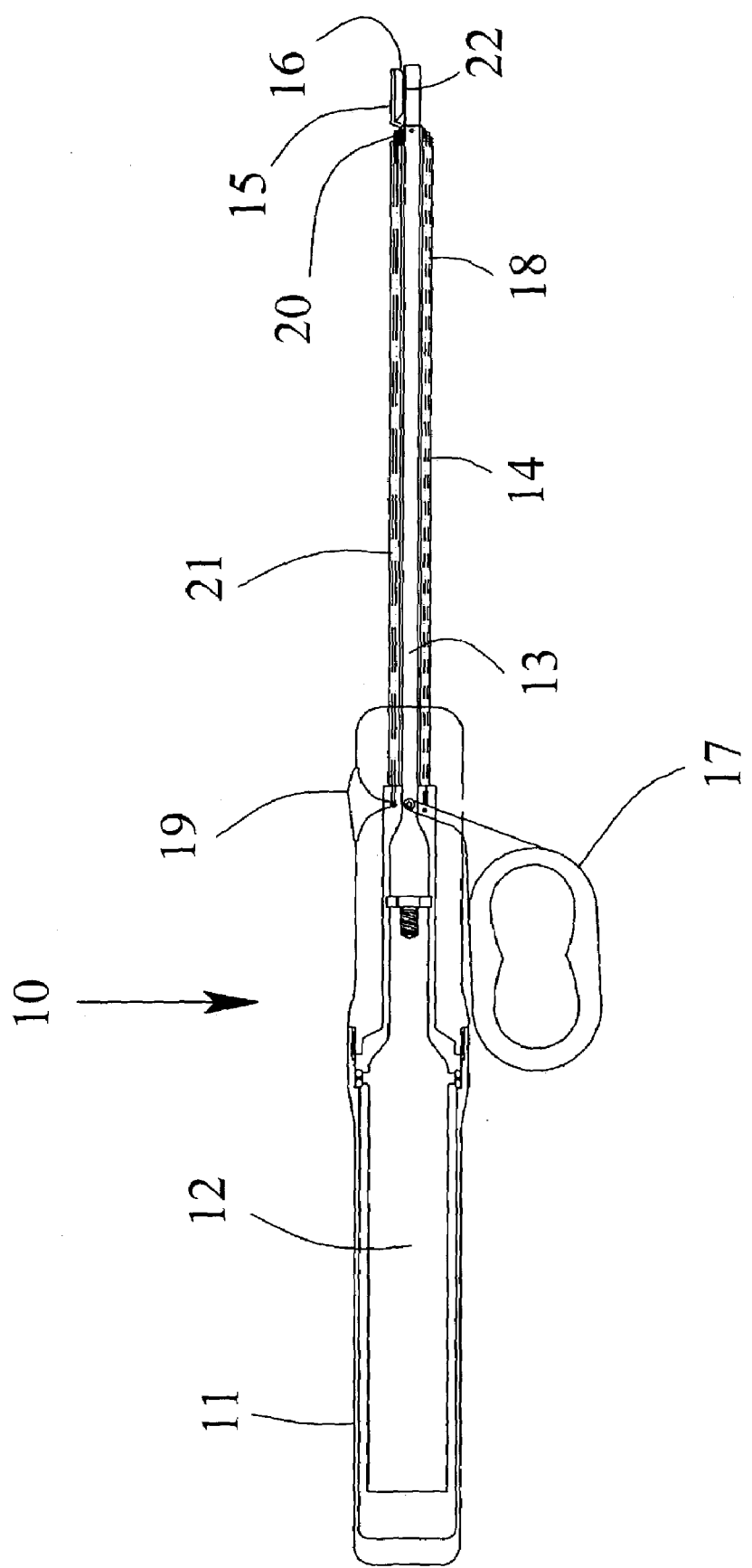
FIG. 1b is a partial cut-away, side view of one embodiment of the device of the present invention. The drawing depicts the device with the clamp in the closed position and the mechanical cutting tool in a retracted position.
Figure 1C:
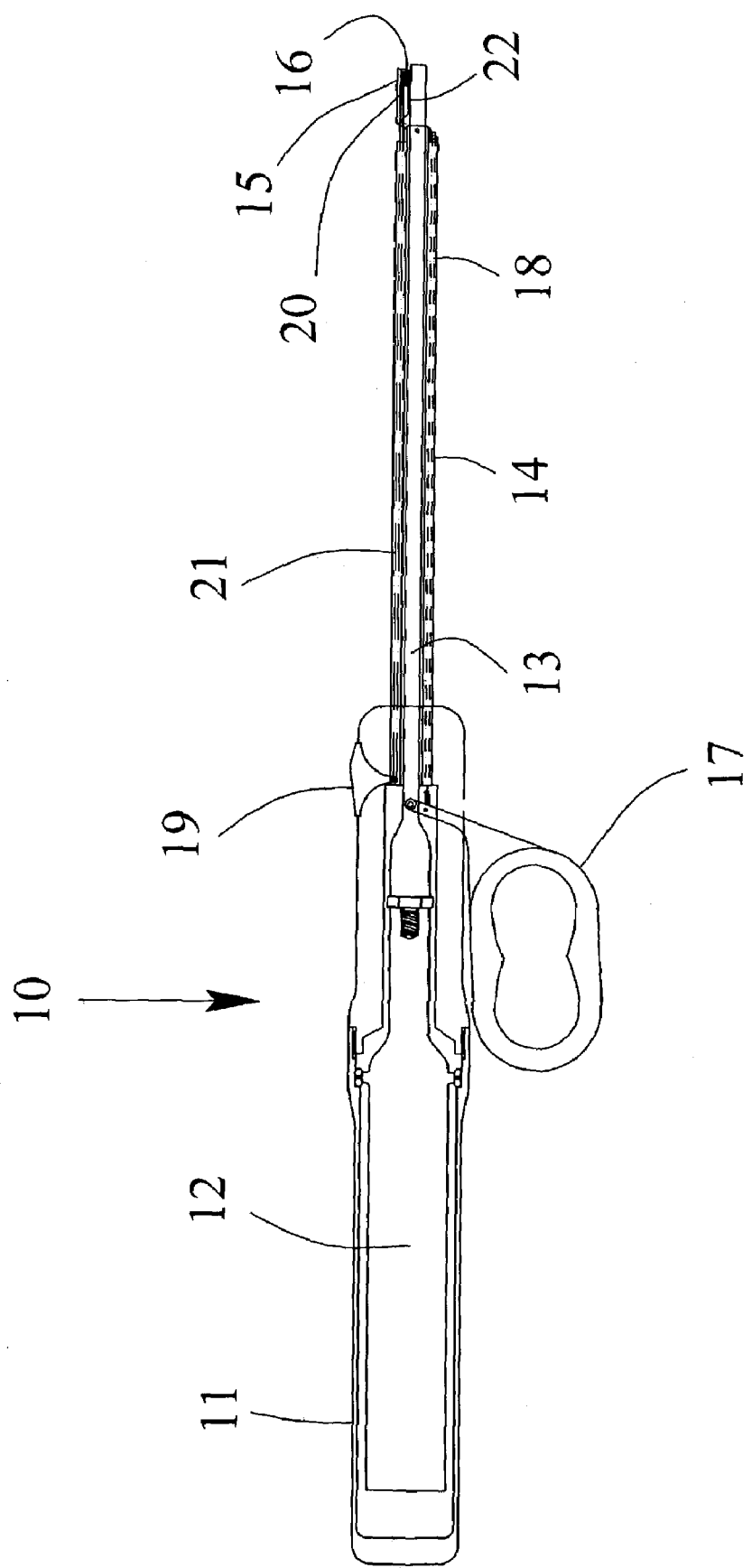
FIG. 1c is a partial cut-away, side view of one embodiment of the device of the present invention. The drawing depicts the device with the clamp in the closed position and the mechanical cutting tool in an advanced position for cutting.
Figure 2:
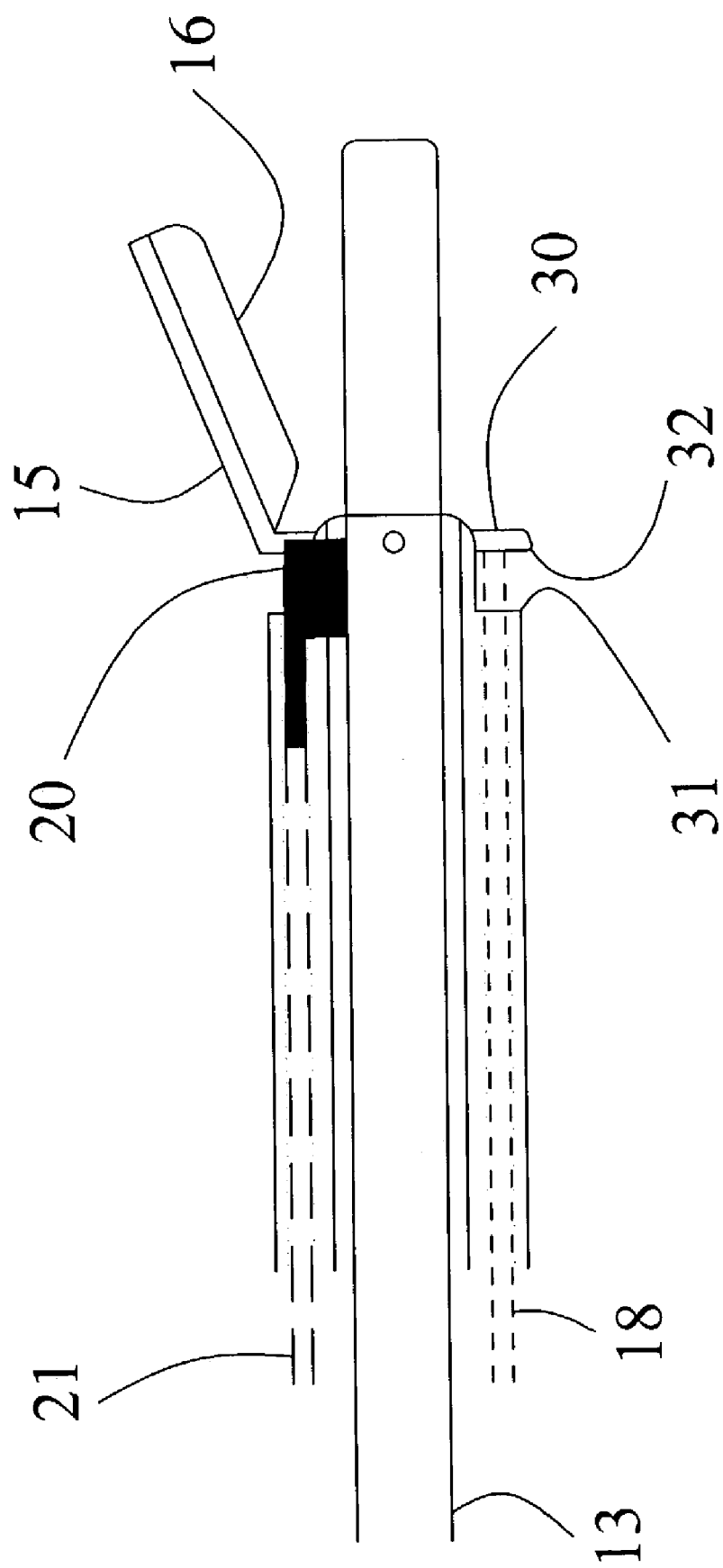
FIG. 2 is detailed partial cut-away, side-view representation of the distal portion of the is ultrasonic device including the electronic applicator, clamp and mechanical cutting tool.

FIG. 2 shows a more detailed side-view of the distal end of the ultrasonic surgical instrument 10 as depicted in FIG. 1a, with the clamp 15 and associated jaw 16 in the open position relative to the ultrasonic applicator 13. Surface 32 of the clamp assembly 30 is separated from surface 31 of the support member 14. The mechanical cutting tool or blade 20 attached to blade connecting rod 21 is in the retracted position. The cutting element 20 can be advanced to cut tissues that have been coagulated between the jaw surface 16 and the ultrasonic applicator 13. (See FIG. 1c.) Thus, the cutting element 20 is advanced and retracted through the clearance between the jaw surface 16 and the ultrasonic applicator 13. In a further embodiment, the clamp 15 and jaw surface 16 may have a vertical slot through with the edge of the blade also passes as it is extended and retracted. This would allow the use of a wider mechanical cutting element and assist in ensuring that the blade cuts all of the tissue held in the space between the jaw surface and the ultrasonic applicator. FIG. 1b shows the same ultrasonic surgical instrument 10 depicted in FIG. 1a, except that the actuation handle 17 has been rotated to the closed position, thereby pulling the clamp transmission rod 18 toward the ultrasonic transducer 12 causing rotation and closing of the clamp 15 relative to the ultrasonic applicator 13. The movement of the transmission rod 18 is limited by a stop, in this the contacting of surface 32 of the clamp housing 30 against surface 31 of the support 14. This occurs so that the jaw face 16 of clamp 15 is "closed" at a predefined distance or clearance from the surface of ultrasonic applicator 13. (See FIGS. 3a through 3c.) This distance can be pre-set and varied by controlling the length of the transmission rod 18. It is within the skill of the art to provide means so that this length can be varied by the physician or an assistant during the course of the surgical procedure without requiring removal of the surgical instrument from the patient. For example, the effective length of the rod from the clamp support 30 to the actuator 17 can be varied by using a rotatable transmission rod threaded into a portion of the handle 11. In FIG. 1b, the cutting blade or tool 20 is in the retracted position.

FIG. 1c illustrates the ultrasonic surgical device 10 of FIG. 1a with the clamp in the closed position and the cutting blade 20 in the extended position. This was accomplished by the movement of actuating slider 10 in a direction toward the distal end of the ultrasonic surgical device, thereby moving the blade connecting rod 21 and the blade 20 in the same direction. As this is accomplished, the tissue held between the clamp 15 and the ultrasonic applicator 13 is cut by the blade 20.

Figure 3:
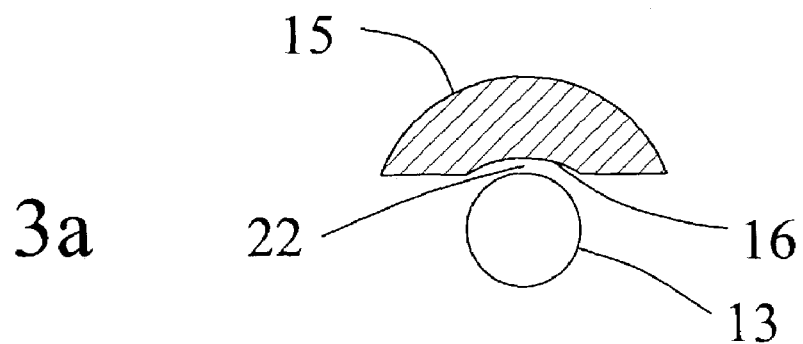
FIG. 3a is an end-on view of the ultrasonic device showing a clamp with a concave jaw surface in the closed position.
FIG. 3b is an end-on view of the ultrasonic device showing a clamp with a convex jaw surface in the closed position.
FIG. 3c is an end-on view of the ultrasonic device showing a clamp with a flat jaw surface in the closed position.
Figure 3:
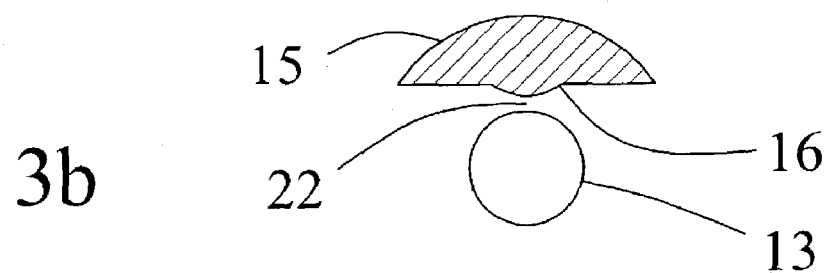
Figure 3:
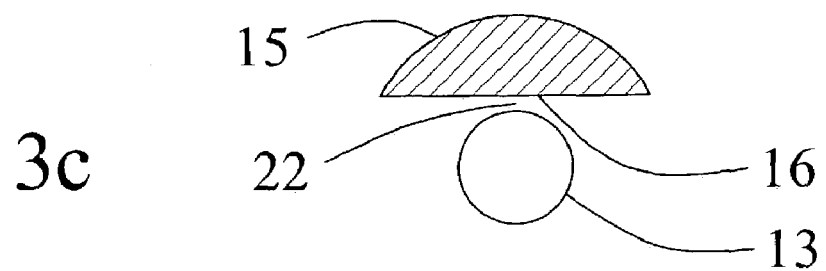

FIGS. 3a through 3c show three different configurations of the jaw surface and the predefined clearance.

FIG. 3a is an end-view showing the ultrasonic applicator 13 and the elongated support member 14 and the clamp 15 in a fully "closed" position. The jaw surface 16 is concave, which provides for improved width of tissue coagulation between the jaw surface 16 and the ultrasonic applicator 13. The predefined clearance 22 is the space between the jaw surface 16 and the ultrasonic applicator 13 when the clamp 15 is closed to its maximum extent, typically between about 0.075 to about 1.9 millimeters, and preferably between about 0.075 and about 0.75 millimeters. Optimal values for the predefined clearance will vary with intended application.

FIG. 3b is an end-view showing the ultrasonic applicator 13 and the elongated support member 14 and the clamp 15 in a fully closed position. The jaw surface 16 is convex which provides for a reduced width of tissue coagulation with improved transition at the edges to the uncoagulated tissue. The predefined clearance 22 is the space between the jaw surface 16 and the ultrasonic applicator 13 when the clamp 15 is fully closed, again typically between about 0.075 to about 1.9 millimeters, and preferably between about 0.075 and about 0.75 millimeters. Optimal values for the predefined clearance will vary with intended application.

FIG. 3c is an end-view showing the ultrasonic applicator 13 and the elongated support member 14 and the clamp 15 in a fully closed position. The jaw surface 16 is flat which provides for a combination of the results obtained with shapes as shown in FIGS. 2a and 2b. The predefined clearance 22 is the space between the jaw surface 16 and the ultrasonic applicator 13 when the clamp 15 is fully closed, typically between about 0.075 to about 1.9 millimeters, and preferably between about 0.075 and about 0.75 millimeters. Optimal values for the predefined clearance will vary with intended application.

Figure 4:
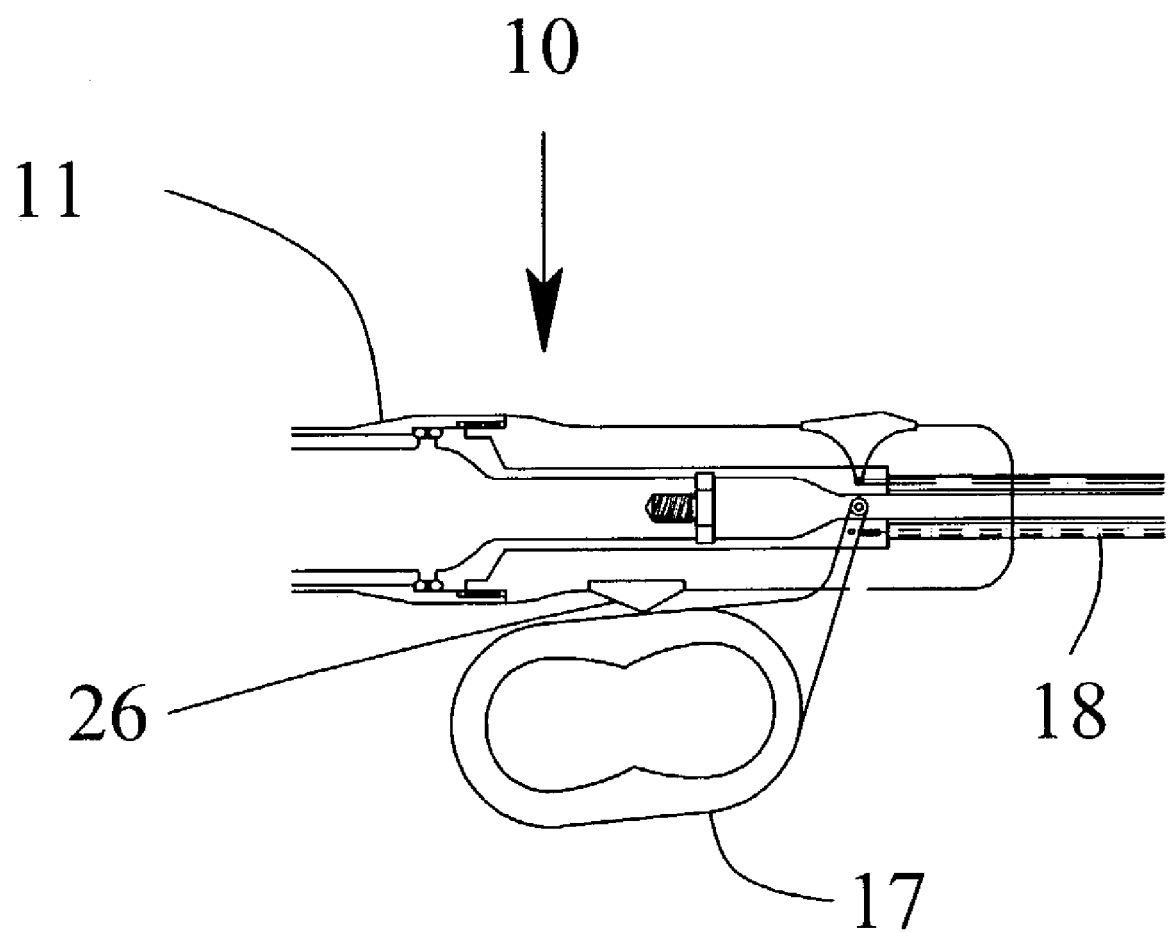
FIG. 4 is a partial cut-away, side-view of one embodiment of the device of the present invention in which the stop for establishing the pre-defined clearance is located on the handle of the ultrasonic device.

The pre-determined clearance between jaw 16 of clamp 15 and ultrasonic applicator 13 can be established in a number of ways. As depicted in FIGS. 1a through 1c and in FIG. 2 this can be established by a stop of clamp housing surface 32 against surface 31 of the support. Other mechanical stops can be used. One such stop is depicted in FIG. 4, which illustrates an ultrasonic surgical device as in FIG. 1a. In this case, however, the stop is physical element 26 extending from the handle 11 and prohibiting closure of actuator 17 against the housing. This replaces the contacting of surfaces 31 and 31 as the stop mechanism. One skilled in the art, would know how to make the effective length of stop 26 variable, so that the predetermine separation 22 between the jaw and applicator can also be varied. For example, the stop 26 could be screwed within a limited range into a hole in the handle 11 so that it could be effectively lengthened or shortened as desired. Other techniques for establishing a predefined clearance between the jaw 16 and the ultrasonic applicator 13 would be known to one skilled in the art and could be substituted for the examples described herein.

The present invention also provides an improved method for the surgical coagulation of animal tissue including locating a portion of the animal tissue between: (a) an ultrasonic applicator having a generally round cross-section with a diameter between approximately 2 and 6 millimeters to provide a broad surface for coagulation and to avoid cutting of the animal tissue and (b) a clamp located adjacent the ultrasonic applicator. The clamp is then moved toward the ultrasonic applicator to a predefined clearance of between about 0.075 to about 1.9 millimeters, and preferably between about 0.075 and about 0.75 millimeters, from the ultrasonic applicator to provide a zone for tissue flow and coagulation. Ultrasonic vibrations are then applied to the clamped tissue via the ultrasonic applicator sufficient to cause coagulation of the tissue. If desired the tissue can then be cut with a separate mechanical cutting tool as illustrated, for example, in the drawings and description herein.

As previously noted the device and method of the present invention are particularly useful in separating and maximizing each of the coagulation and cutting functions. It also provides a convenient way for the surgeon to know at all times the position of the clamp relative to the ultrasonic applicator and the position of the cutting element or blade. Thus, the surgeon can easily monitor and focus on these tasks.

The description and drawings contained herein disclose illustrative embodiments of the invention. Given the benefit of this disclosure, those skilled in the art will appreciate that various modifications, alternate constructions, and equivalents may also be employed to achieve the advantages of the invention. For example, given the benefit of this disclosure, those skilled in the art will be able to implement various forms of the clamp, the stop and the mechanical cutting tool within the spirit of the invention. Therefore, the invention is not to be limited to the description and illustrations contained herein, but is defined by the following claims.

The invention claimed is:

1. An ultrasonic surgical apparatus for the coagulation of animal tissue having a handle for manipulation by a surgeon, an ultrasonic transducer for generating ultrasonic vibration, and an ultrasonic applicator attached to the ultrasonic transducer and extending from the handle for delivery of ultrasonic vibrations to the animal tissue, wherein said apparatus further comprises:

a distal portion on the ultrasonic applicator having a generally round cross-section with a diameter between approximately 2 and 6 millimeters to provide a broad surface for coagulation and to avoid cutting of the animal tissue;

an elongated support member releasably attached to the surgical handle and extending to the distal portion of the ultrasonic applicator;

a movable jaw with a jaw surface attached to the elongated support member adjacent the distal portion of the ultrasonic applicator for movement toward said distal portion to a closed position at a predefined clearance of between about 0.075 to about 1.9 millimeters, from said distal portion, wherein the movable jaw is configured to grasp and hold the animal tissue during coagulation while allowing the animal tissue to flow and coagulate; and a stop for establishing the predefined clearance.

2. The ultrasonic surgical apparatus of claim 1 wherein the predefined clearance is between about 0.075 and about 0.75 millimeters.

3. The ultrasonic surgical apparatus of claim 2 wherein the jaw surface in the closed position is generally parallel with the surface of the elongated support member.

4. The ultrasonic surgical device of claim 2 wherein the jaw surface is concave.

5. The ultrasonic surgical device of claim 2 wherein the jaw surface is convex.

6. The ulstrasonic surgical device of claim 2 wherein the jaw surface is flat.

7. The ultrasonic surgical device of claim 2 wherein the stop is located on the elongated support member.

8. The ultrasonic surgical device of claim 2 wherein the stop is located on the handle of the ultrasonic surgical device.

9. The ultrasonic surgical device of claim 2 wherein the predetermined clearance may be varied without requiring removal of the ultrasonic surgical device from the patient during a medical procedure.

10. An ultrasonic surgical apparatus for the treating of animal tissue having a handle for manipulation by a surgeon an ultrasonic transducer for generating ultrasonic vibration, and an ultrasonic applicator attached to the ultrasonic transducer and extending from the handle for delivery of ultrasonic vibrations to the animal tissue, wherein said apparatus further comprises:

a distal portion on the ultrasonic applicator having a generally round cross-section with a diameter between approximately 2 and 6 millimeters to provide a broad surface for coagulation and to avoid cutting of the animal tissue;

an elongated support member releasably attached to the surgical handle and extending to the distal portion of the ultrasonic applicator;

a movable jaw with a jaw surface attached to the elongated support member adjacent the distal portion of the ultrasonic applicator for movement toward said distal portion to a closed position at a predefined clearance of between about 0.075 to about 1.9 millimeters from said distal portion, wherein the movable jaw is configured to grasp and hold the animal tissue during coagulation while allowing the animal tissue to flow and coagulate as the animal tissue is heated by vibration of the ultrasonic applicator;

a stop for establishing the predefined clearance; and a mechanical cutting device for movement parallel to the ultrasonic applicator to cut the animal tissue located between the ultrasonic applicator and the clamp.

11. The ultrasonic surgical apparatus of claim 10 wherein the predefined clearance is between about 0.075 and about 0.75 millimeters.

12. The ultrasonic surgical apparatus of claim 11 wherein the jaw surface in the closed position is generally parallel with the surface of the elongated support member.

13. The ultrasonic surgical device of claim 11 wherein the jaw surface is concave.

14. The ultrasonic surgical device of claim 11 wherein the jaw surface is convex.

15. The ultrasonic surgical device of claim 11 wherein the jaw surface is flat.

16. The ultrasonic surgical device of claim 11 wherein the stop is located on the elongated support member.

17. The ultrasonic surgical device of claim 11 wherein the stop is located on the handle of the ultrasonic surgical device.

18. The ultrasonic surgical device of claim 11 wherein the predetermined clearance may be varied without requiring removal of the ultrasonic surgical device from the patient during a medical procedure.

19. The ultrasonic surgical device of claim 11 wherein the mechanical cutting device is a blade.

20. A method for the surgical coagulation of animal tissue comprising:

locating a portion of the animal tissue between
an ultrasonic application having a generally round cross-section with a diameter between approximately 2 and 6 millimeters to provide a broad surface for coagulation and to avoid cutting of the animal tissue; and
a clamp located adjacent the ultrasonic tissue;

moving the clamp toward the ultrasonic applicator to a predefined clearance of between about 0.075 to about 1.9 millimeters from the ultrasonic applicator to grasp and hold the desired tissue during coagulation while providing a zone for tissue flow and coagulation, wherein the predetermined clearance is established by a stop; and applying ultrasonic vibrations to the portion of the tissue via the ultrasonic applicator sufficient to cause coagulation of the tissue.

21. The method of claim 20 wherein the predefined clearance is about 0.075 and about 0.75 millimeters.

22. The method of claim 21 wherein the predetermined clearance may be varied without requiring removal of the ultrasonic surgical device from the patient during a medical procedure.

23. A method for surgically treating animal tissue with minimal bleeding comprising:

locating the animal tissue between
an ultrasonic applicator having a generally round cross-section with a diameter between approximately 2 and 6 millimeters to provide a broad surface for coagulation and to avoid cutting of the animal tissue;

moving the clamp toward the ultrasonic applicator to a predefined clearance of between about 0.075 to about 1.9 millimeters from the ultrasonic applicator to grasp and hold the animal tissue during coagulation while providing a zone for tissue flow and coagulation as the animal tissue is heated by vibration of the ultrasonic applicator, wherein the predetermined clearance is established by a stop;

applying ultrasonic vibrations to the animal tissue via the ultrasonic applicator sufficient to cause coagulation of the animal tissue; and cutting said tissue after it has been coagulated using a mechanical cutting device.

24. The method of claim 23 wherein the predefined clearance is between about 0.075 and about 0.75 millimeters.

25. The method of claim 24 wherein the predetermined clearance may be varied without requiring removal of the ultrasonic surgical device from the patient during a medical procedure.

26. The method of claim 24 wherein the mechanical cutting device is a blade.

* * * * *